United States Patent [19]

Blake, III et al.

[11] Patent Number: 4,863,424
[45] Date of Patent: Sep. 5, 1989

[54] TUBULAR MEDICAL DEVICE AND METHOD OF MAKING AND USING THE SAME

[76] Inventors: Joseph W. Blake, III, 88 Main St., New Canaan, Conn. 06840; Jack W. Kaufman, 357 Frankel Blvd., Merrick, N.Y. 11566

[21] Appl. No.: 553,200

[22] Filed: Nov. 18, 1983

[51] Int. Cl.⁴ .......................................... A61M 29/02
[52] U.S. Cl. ...................................... 604/54; 604/103; 604/247; 604/266; 604/270; 604/271; 604/282
[58] Field of Search ............... 604/236, 246, 169, 213, 604/247, 256, 103, 270, 271, 266, 267, 282, 96, 49, 54

[56] References Cited

U.S. PATENT DOCUMENTS

| | | | |
|---|---|---|---|
| 2,819,718 | 1/1958 | Goldman | 604/96 |
| 3,058,472 | 10/1962 | Thornton | 604/256 |
| 4,119,094 | 10/1978 | Micklus et al. | 128/132 R |
| 4,410,320 | 10/1983 | Dykstra et al. | 604/270 |
| 4,419,095 | 12/1983 | Mebergall et al. | 604/96 |

FOREIGN PATENT DOCUMENTS

| | | | |
|---|---|---|---|
| 158740 | 8/1954 | Australia | 604/247 |
| 1428766 | 3/1976 | United Kingdom | 604/96 |

*Primary Examiner*—Michael H. Thaler
*Attorney, Agent, or Firm*—Lackenbach Siegel Marzullo & Aronson

[57] ABSTRACT

This invention relates generally to a tubular medical device, and more particularly to a tubular medical device for fluid feeding to or fluid drainage from a body cavity. The invention describes both a device and a method of making a device that comprises an elongated flexible primary tube forming a lumen having an open end, a secondary tube concentrically surrounding and spaced from the primary tube and extending between the open end and a position spaced from the open end. The primary and secondary tubes have an integral joining portion at the open end. The primary and secondary tubes form a chamber that is sealably closed and filled with a heavy metal so that a weighted tip element, or bolus is formed. Alternatively, the chamber may be pressurized and expanded to form a balloon element by way of a side tube affixed to the primary tube and connected at one end to a source of pressurized air and at the other end to a position within the chamber.

25 Claims, 3 Drawing Sheets

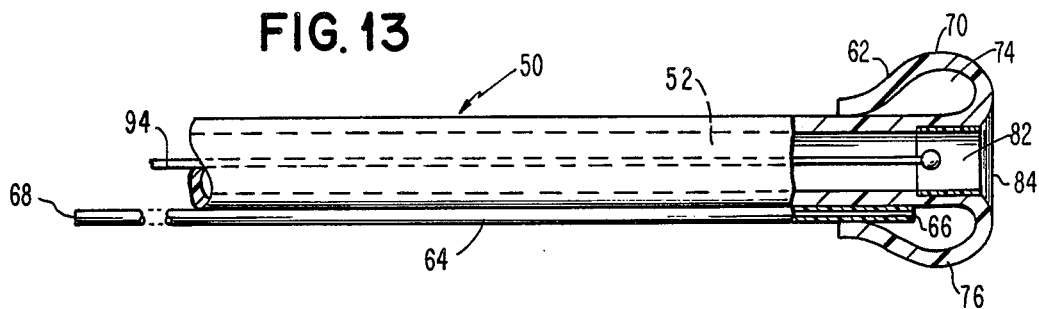
FIG. 13
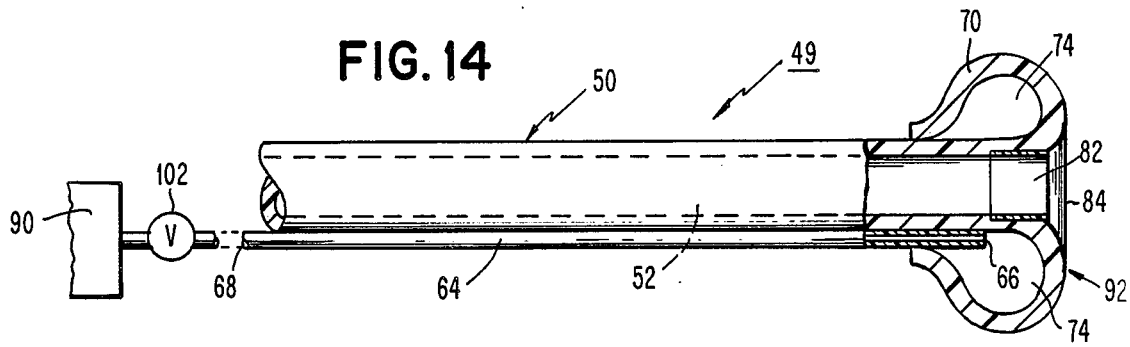
FIG. 14
FIG. 15
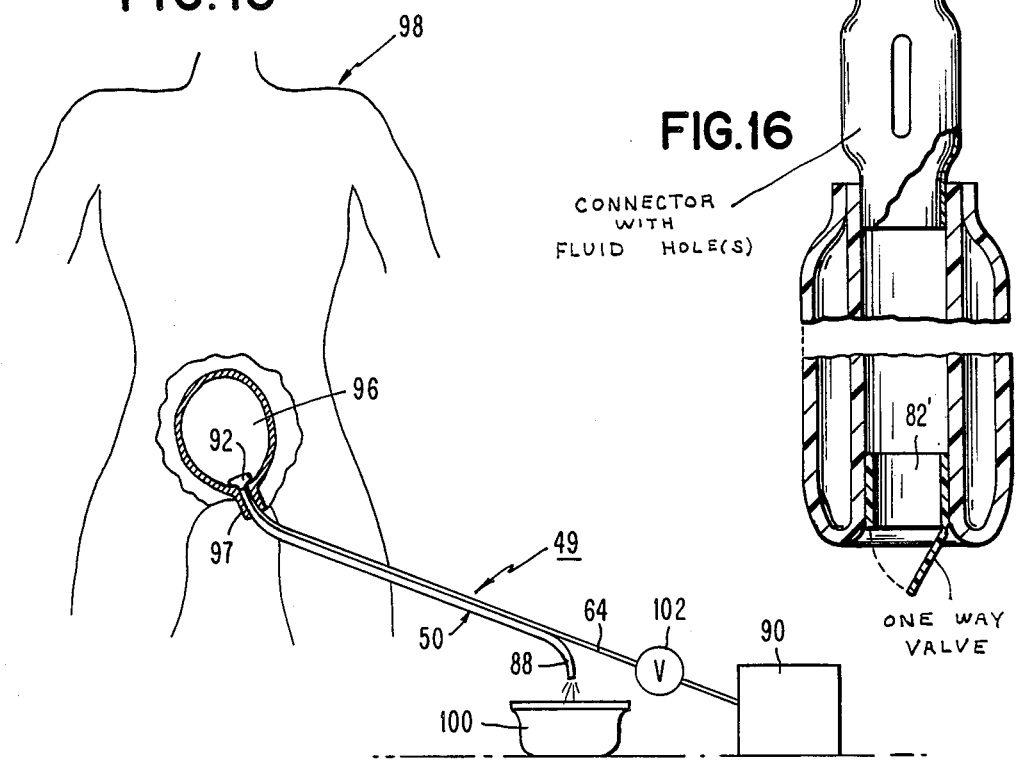
FIG. 16
CONNECTOR WITH FLUID HOLE(S)
ONE WAY VALVE

TUBULAR MEDICAL DEVICE AND METHOD OF MAKING AND USING THE SAME

BACKGROUND OF THE INVENTION

The present patent invention relates generally to a tubular medical device, and more particularly to a tubular medical device for gastroenteric fluid feeding to or fluid drainage from a body cavity.

Enteric feeding tubes deliver nutrients directly into the stomach of a patient. This common method of sustaining a patient is an alternative to intravenous feeding. The forward end of the elongated feeding tube is weighted by means of placing a heavy metal into a chamber at the forward end of the feeding tube, which is then sealed by sealing itself onto the tube to form a bolus.

The bolus and the tube are pushed through the nasal area of the patient down the esophagus into the stomach partly by the aid of peristaltic action of the esophagus and partly by the aid of the weight and shape of the bolus. The tube is rigidized somewhat during the insertion process with a stainless steel stylet, which is placed in the tube and removed when the bolus reaches the stomach area. The inlet end of the tube is attached to an enteric feeding bag containing nutrients, which are gravity fed or preferably metered through a pump from the bag to the stomach.

In the prior art devices, nutrient passes through holes formed in the enteric tube above the bolus, which is blind. A pocket is formed between the bolus and the hole nearest the bolus, where the nutrients stagnate. Kinking at the eyelets, or holes, also occurs. Such a prior art device is manufactured by Biosearch Medical Products, Inc, Somerville, N.J. and identified as EN-TRIFLEX ® feeding tube.

An enteric feeding device that is free of a nutrient pocket is made by the Corpak Company. The device as manufactured by Corpak, however, uses a conventional bolus as is used by Biosearch. The Corpak device has an enlargement or "pill-shaped" T-connection configured between the enteric tube and the bolus, which would be expected to cause problems during insertion.

Enteric draining tubes are also used which, instead of a weighted bolus tip, have a forward area that can be blown up by way of action of an inner tube in the drain tube that exits through a hole in the drain tubes and balloons outside of the wall of the enteric tube. The balloon tends to position the draining device in the area designated. For example, the balloon portion of a urethra catheter is inflated in the bladder of the patient so that the catheter does not slide from the bladder along the urethra. Balloon catheters that are inserted into veins are known and have varied purposes, such as locking the catheter into a position against the walls of the vein, breaking blood clots, and so on.

Prior art for balloon catheters have the balloon extending through a hole in the side of the catheter tube, rather than at the front, where for maneuvering purposes positioning would be desirable.

The prior art devices for both enteric feeding and draining and catheters of the balloon variety are clearly in need of an improvement, which, however, has not been forthcoming heretofore.

SUMMARY OF THE INVENTION

Accordingly, it is an object of the present invention to overcome the disadvantages of the prior art, and to provide an improved medical device of the type capable of fluid feeding to or fluid drainage from a body cavity.

Another object of the invention is to provide a device of the kind under discussion, which has an enlarged tip, which is capable of receiving a tip-positioning substance and which surrounds the central channel or passage, that is, the lumen of the tubular device.

Yet another object of the invention is to provide a device of the kind under discussion that is unique and inexpensive to manufacture.

Yet another object of the invention is to provide a device having a weighted bolus at the tip that surrounds the lumen of the tube so that the lumen opens at the end of the bolus.

Yet another object of the invention is to provide a device having a balloon at the tip that surrounds the lumen of the tube so that the lumen opens at the end of the balloon and prevents the device from slipping from a body cavity of the patient.

Still further objects of the invention are to provide such an improved tip element that combines a tip element and lumen outlet that does not exist in the prior art one-piece tubular element, or from a one-piece tubular element affixed to a tube connected to a source of pressurized air.

In keeping with these objects, and with others that will become apparent hereinafter from the accompanying description, a tubular medical device is provided that is applied to both fluid feeding into or fluid drainage from a body cavity of a patient. The device comprises an elongated flexible primary tube having a central lumen, or passage. The primary tube has a tip, or end, at which the passage opens. A secondary tube concentrically surrounds the primary tube and extends between the open end and a position spaced from the open end. The secondary tube is unitary with the primary tube and sealably connected with the primary tube at the position spaced from the open end. The secondary tube is spaced from the primary tube and forms with the primary tube a sealed chamber. A substance is positioned in the chamber so that the tip of the device can be positioned in the cavity of the patient. The outer surface of the secondary tube has a hydrophilic coating. The primary tube and the secondary tube are made of a radio opaque material. The substance in the chamber is a heavy metal, such as liquid mercury or tungsten granules.

The present invention can further include a flexible side tube affixed to the outer surface of the primary tube and extended into the chamber. The secondary tube is sealably connected to the primary tube at the sealing position around the secondary tube. The side tube has opposed side tube ends, one of the ends being positioned in the chamber. The device in this embodiment further includes a source of pressurized air, and the other of the side tube ends is connected to the source of pressurized air. The secondary tube in this embodiment is elastic and is expanded when the chamber is expanded under pressure from the pressurized air, so that the chamber forms a balloon, in contrast to a weighted bolus.

The present invention further provides a method of making a tubular medical device for fluid input or outtake from a body cavity of a patient. The method includes treating the entire inner surface of the overall tube or of just the heat expandable tip portion, or front end portion, of the elongated radio opaque flexible primary tube with a hydrophilic coating. The next step is expanding the front end portion by heating and pressurizing the front end portion into a secondary tube having a diameter greater than the diameter of the primary tube. The following step is concentrically everting the secondary tube back around and spaced from the primary tube, wherein the hydrophilic coating is carried over to the outer surface of the secondary tube. The primary tube and the secondary tube form a chamber defined by the outer surface of the primary tube, the inner surface of the secondary tube, and the unitary joining portion at the new front end of the device. The chamber has a circular opening at the rear end of the secondary tube, the rear end being spaced from the joining portion at the tip of the device. The following step is placing a substance into the chamber through said opening; the substance is for positioning the front end of the device in the body cavity of the patient. The next step is sealing the chamber at the circular opening by shrinking the rear end of the secondary tube and sealably joining the rear end of the secondary tube with the outer surface of the primary tube. The substance placed in the chamber is a heavy metal such as liquid mercury or tungsten granules. The primary and secondary tubes are made of a radio opaque material and urethane with an additive is suitable.

The above described method can alternatively include the steps of affixing an elongated flexible side tube having inlet and outlet ends to the outer surface of the primary tube so that the outlet end of the secondary tube is positioned at a distance from the joining portion so that when the secondary tube is everted as described above, the outlet end of the side tube is located with the chamber. The inlet end of the side tube is cemented to a source of pressurized air. After the tip of the device has been inserted into the body cavity of the patient, the chamber is filled with pressurized air so that the secondary tube is expanded to form a balloon.

The novel features that are considered to be characteristic of the invention are set forth in particular in the hereto appended claims. The improved device itself, however, together with details of its construction and the best mode of operation currently known to the applicant, as well as additional features and advantages of the device and of the method, will be best understood upon a perusal of the following detailed description of specific although purely exemplary embodiments with references to the accompanying drawings.

BRIEF DESCRIPTION OF THE DRAWINGS

FIG. 13 is a partially sectioned side view of the completed medical device shown in FIG. 12, but with a stylet inserted into the lumen;

FIG. 14 is a partially sectioned side view of the device shown in FIG. 13 with the secondary tube connected to a source of pressurized air and tip of the device ballooned; and FIG. 15 is a schematic representation of the device shown in FIG. 14 positioned in the bladder of a patient; and FIG. 16 is a partially sectioned side view of alternate constructions of the tubular device of the invention.

DESCRIPTION OF THE PREFERRED EMBODIMENTS

Figure 1:
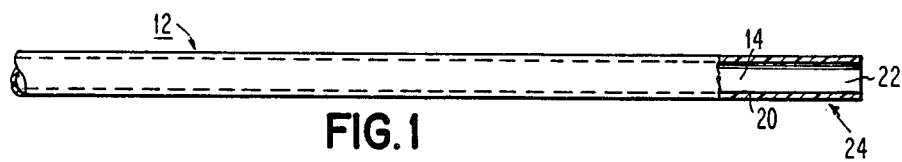
FIG. 1 is a partially sectioned side view of a primary tube for making the tubular device of the present invention.

Reference is now made to the drawings in which identical or similar parts are designated by the same reference numerals throughout.

As shown therein, a tubular medical device 10 is best illustrated in its various steps of manufacture in FIGS. 1 through 5. A description of these steps will be made in sequence according to the figures indicated beginning with FIG. 1 and culminating in device 10 in FIG. 5.

As shown in FIG. 1, an elongated primary tube 12 forms a central passage, or lumen, 14 that has an opening 16 on the front end 18 of tube 12. Primary tube 12 is made of a flexible, radio opaque material, such as urethane. The diameter of lumen 14 will vary according to the patient, the flow of liquid nutrient being sent through lumen 14 and may be influenced by other factors. Common lumen sizes are sizes 6,8,10 and 12 French, with, for example, 12 French being 109 cm.

Figure 2:
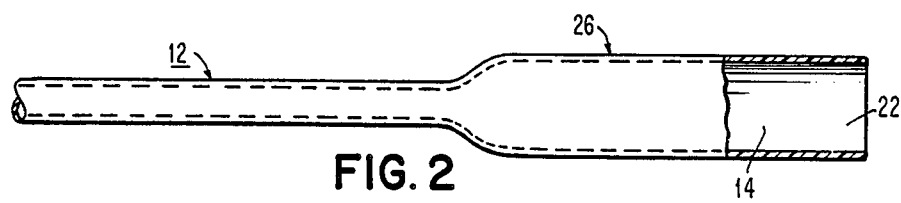
FIG. 2 is a partially sectioned side view of the tube after the tip portion thereof has been heated and expanded to form a secondary tube.

The inner surface 20 of lumen 14 is treated, or layered, with a hydrophilic coating 22, indicated by a spotted surface in FIGS. 1 and 2 and generally in FIGS. 3–6.

The primary tube 12 is made of a material capable of being stretched when heated. FIG. 2 illustrates primary tube 12 after its front end 24 has been heat treated and expanded by a pressuring, or stretching, which are methods well known in the art. However, a unique and novel method for making the tubular medical device of the invention comprises everting the front end 24 of the primary tube #12 so that the hydrophilic coating 22 is then disposed on the outside of the primary tube 12. Thus, there is now formed a secondary tube 26 having a diameter larger than the diameter of lumen 14 of the elongated primary tube 12.

The hydrophilic coating 22 which is provided along the inner surface of lumen 14 by methods well known in the art do not form a part of the present invention. But such a hydrophilic coating on both the inside and outside diameters of the lumen ensure smooth tip introduction into the GI tract and easier vasogastric passage, as well as assisting in removal of the stylet 44. The hydrophilic coating renders the tube or lumen surfaces slick to feel and thus minimize and/or entirely eliminate the need for coating the tube with a lubricating jelly. Such a coating is known from U.S. Pat. Nos. 4,100,309 and 4,119,094 assigned to Biosearch Medical Products, Inc. of Raritan, N.J. It should also be noted that with the embodiment of FIG. 16 just the separate front end portion of primary tube 12 can be of the urethane material, whereas the tube 12 could then be of another suitable material. Also, the plastic material may be of polyurethane, or a co-polymer of silicone or polyurethane. A urethane composition is preferred since such material is of sufficient strength, biocompatible, kink resistant and resistant to gastric juices.

Figure 3:
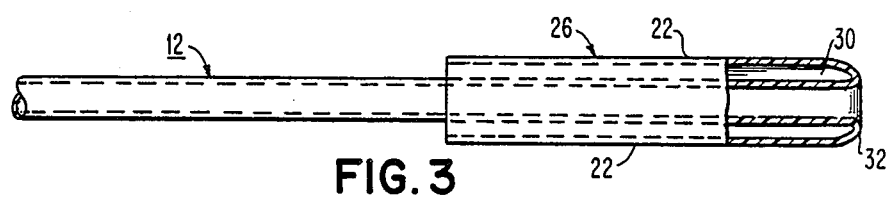
FIG. 3 is a partially sectioned side view of showing the secondary tube everted back around the primary tube to form a chamber.

FIG. 3 illustrates the result of having concentrically everted secondary tube 26 back-around and spaced from primary tube 12. Hydrophilic coating 22 is carried over to the outer surface 28 of secondary tube 26. Primary tube 12 and secondary tube 26 form a chamber 30 defined by, first, primary tube 12; second, a unitary connection between primary tube 12 and secondary tube 26 at joining portion 32; and third, secondary tube 26. Chamber 30 has a donut-like circular opening 34 at the rear end 36 of secondary tube 26 which is spaced from joining portion 32, which in turn defines an opening for the chamber 30.

Figure 4:
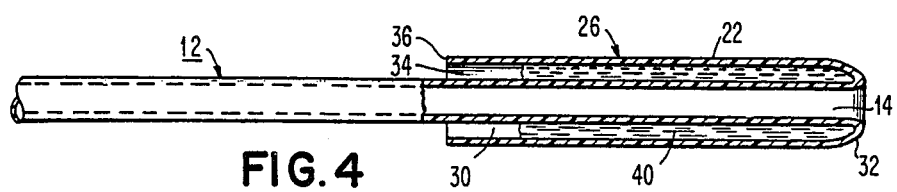
FIG. 4 is a partially sectioned side view showing the chamber filled with a heavy metal.

FIG. 4 illustrates a heavy metal 40 having been placed into chamber 30 through opening 34. The heavy metal preferably is mercury or tungsten granules, but use of other heavy metals could be employed in the weighted tip.

Figure 5:
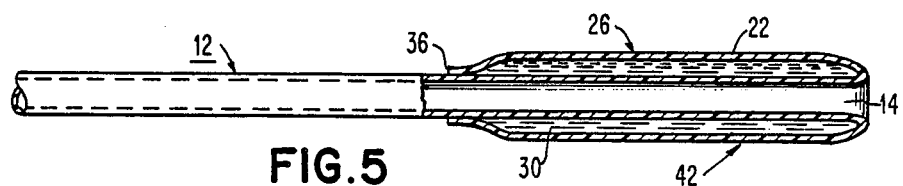
FIG. 5 is a partially sectioned side view showing the secondary tube sealed to the primary tube so as to seal the chamber containing the heavy metal.

FIG. 5 illustrates chamber 30 having been sealed at rear end 36 at closing circular opening 34 preferably by shrinking rear end 36 of secondary tube 26 and heat joining secondary tube 26 to the outer surface of primary tube 12. Heavy metal 40 is thus sealed in chamber 30 forming a tip element, or bolus, 42, which has a hydrophilic coating 22 and lumen 14 extending through the tube 12. FIG. 5 illustrates device 10 as completed and ready for use.

Figure 6:
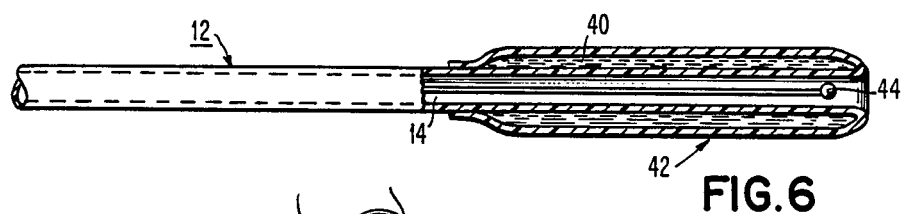
FIG. 6 is a partially sectioned side view of the completed medical device and showing a stylet inserted into the lumen of the device.
Figure 7:
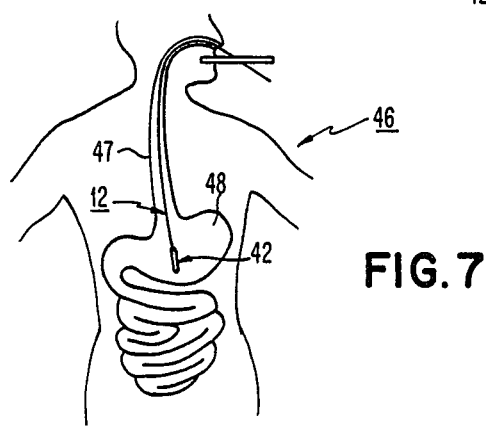
FIG. 7 is a schematic representation showing the tubular device positioned in the stomach of a patient.

FIG. 6 illustrates device 10 with bolus 42 and a stylet 44 extending through lumen 14. Stylet 44 is an aid primarily for stiffening the tube 12 and it aids in guiding bolus 42 through the nose of a patient 46 down the esophagus 47 and into the stomach 48, as illustrated schematically in FIG. 7.

Another embodiment of the present invention which is intended for fluid draining from a body cavity of a patient is shown in FIGS. 8 through 13, which are illustrative of the steps of manufacture to achieve the finished device 49 in FIG. 14. The steps of manufacture are analogous to the steps of FIGS. 1 through 5, but each step will be fully set forth with numerals distinct from those of the first embodiment in FIGS. 1-5.

Figure 8:
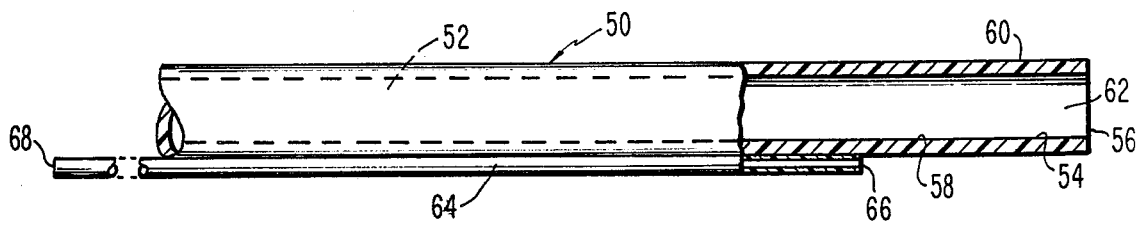
FIG. 8 is a partially sectioned side view of another embodiment of the present invention including a side air tube affixed to the outside of a primary tube; which is to be made into the device of the invention.

As shown in FIG. 8, an elongated primary tube 50 forms a central passage, or lumen, 52 that has an opening 54 on the front end 56 of tube 50. Primary tube 50 is made of a flexible, radio opaque material, that, in addition, is elastic and capable of being stretched to form a bolus end which can be inflated.

The diameter of lumen 52 will vary according to the patient, the flow of fluid from the body cavity, and other factors. The inner surface of lumen 52 is treated, or layered, with a hydrophilic coating 62, which is indicated by a spotted surface in FIG. 8 and 9 and generally in FIGS. 10-13.

An elongated flexible side tube 64 having opposed outlet and inlet ends 66 and 68, respectively, is affixed to the outer surface of primary tube 50. Inlet end 68 is positioned at a position spaced at a distance from front end 56.

Figure 9:
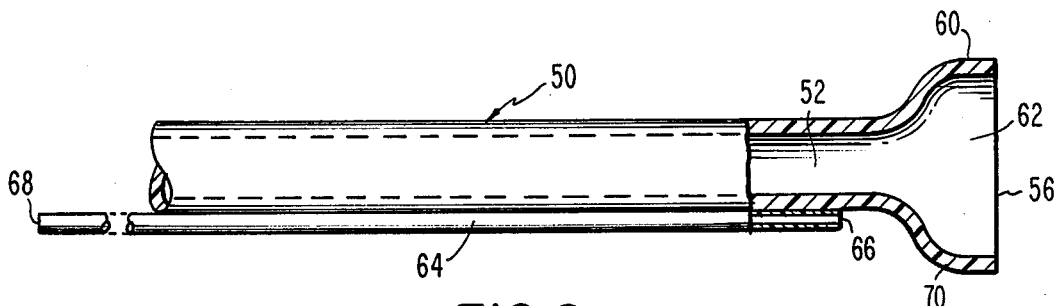
FIG. 9 is a partially sectioned side view of the tube shown in FIG. 8 after the secondary tube has been formed.

The front end portion 60 at least of primary tube 50 is made of a material capable of being stretched when heated, but it is preferred the entire tube 50 is of the same material. It is noted here that the length of front end portion 60 is less than the analogous front end portion 24 of the embodiment of FIGS. 1-5, for reasons which will become apparent. FIG. 9 illustrates primary tube 50 after its front end portion 60 has been heat treated and expanded by a pressuring or stretching method known in the art to form a secondary tube 70 having a diameter larger than the diameter of lumen 52 of primary tube 50.

Figure 10:
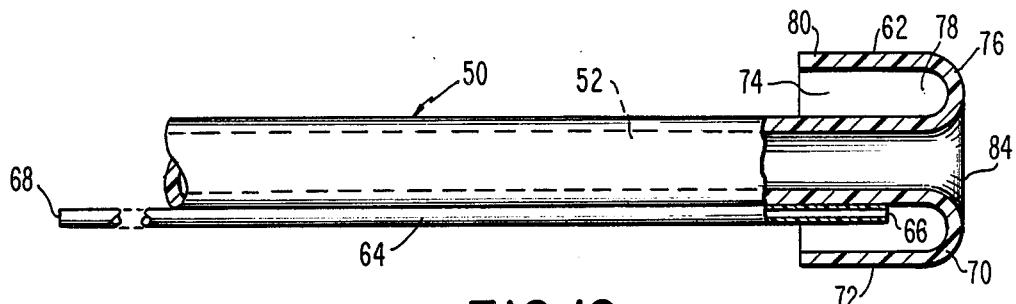
FIG. 10 is a partially sectioned side view of the tube shown in FIG. 9 with the secondary tube everted back around the primary tube.

FIG. 10 illustrates the result of having concentrically everted secondary tube 70 back around and spaced from primary tube 50. Hydrophilic coating 62 likewise is carried over to the outer surface 72 of secondary tube 70. Primary tube 50 and secondary tube 70 form a chamber 74 defined by, first, primary tube 70; second, a unitary connection between primary tube 50 and secondary tube 70 at joining portion 76; and, third, secondary tube 70. Chamber 74 has a donut-like circular opening 78 at the rear end 80 of secondary tube 70, which is spaced at a distance from joining portion 76, which in turn defines an opening 84 of lumen 52. Outlet end 66 of side tube 64 is positioned within chamber 74.

Figure 11:
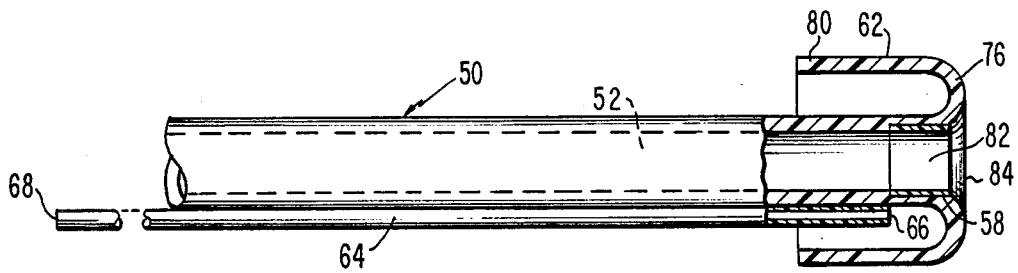
FIG. 11 is a partially sectioned side view of the tube shown in FIG. 10 with a support ring inserted into the lumen and affixed to the inner surface of the lumen at the tip of the device.

FIG. 11 illustrates a stiffening ring inserted into lumen 52 of primary tube 50 and connected to inner surface 58 inwardly from joining portion 76, which in fact is located at new front end 84 of device 49. Stiffening ring 82 is preferably made of a rigid plastic and is suitably heat sealed to inner surface 58. The inner diameter of stiffening ring 82 is preferably of approximately the same diameter as lumen 52 so that there will be no obstruction to fluid flow into new front end 84, which actually is the intake end of primary tube 50, to discharge end 88 (FIG. 15) of primary tube 50, discharge end 88 being located at the opposite end of primary tube 70 from new front end 84 and located outside the body of the patient. Tube 50 is preferably of a flexible material as noted earlier.

Figure 12:
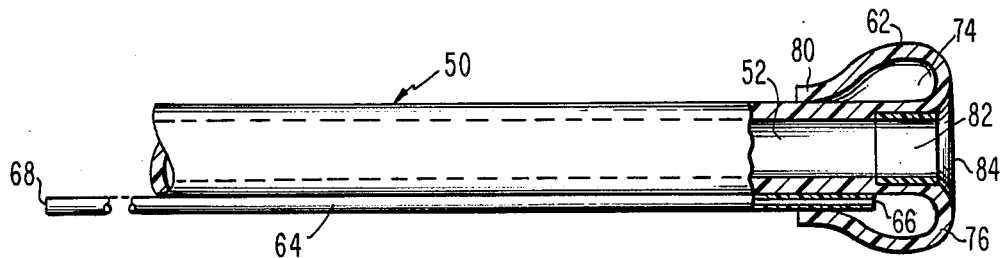
FIG. 12 is a partially sectioned side view of the tube shown in FIG. 11 with the secondary tube affixed to the primary tube around the secondary tube and the side tube so as to seal the chamber.

FIG. 12 illustrates chamber 74 having been sealed at rear end 80 thus closing circular opening 78 preferable by shrinking rear end 80 of secondary tube 70 and heat joining secondary tube 70 to the outer surface of primary tube 50. Rear end 80 is likewise heat sealed to and around side tube 64 so that rear end 80 completely seals chamber 74.

As noted previously, front end portion 60, which is equivalent to secondary tube 70, is profoundly shorter than front end portion 24 of device 10, since it is preferable that balloon element 92 not have the expanded volume that would form if chamber 74 of device 49 were of the same volume as chamber 30 of device 10.

FIG. 13 illustrates a stylet 94 inserted into lumen 52 almost to front opening 84 and generally aligned with chamber 74. It is in this position that primary tube 50 is inserted through a canal similar to the urethra 97 into a body cavity similar to the bladder 96 of a patient 98 as shown in schematic representation in FIG. 15. Discharge end 88 of primary tube 50 is positioned over a receptacle such as basin 100, which receives the fluid drained and/or removed from bladder 96.

FIG. 14 illustrates inlet end 68 of side tube 64 connected to a source of pressurized air 90. Source 90 has been activated so as to pressurize and expand chamber 74 to form balloon element 92, which is analogous to bolus, or tip element, 42 of the prior embodiment of device 10. Balloon element 92 is formed after chamber 74 of primary tube 50 has been positioned in the body cavity, in the example being bladder 96 shown in FIG. 15, where chamber 74 is ballooned via source 90, which is regulated by valve 102 shown as proximal to and downstream of source 90. Balloon element 92 is kept inflated by a method known in the art until device 49 is to be withdrawn, at which time the pressurized air inflation of chamber 74 is terminated and balloon element 92 deflates and device 49 is withdrawn from bladder 96. Balloon element 92 when employed is generally expanded to a volume such that the diameter thereof is greater than say the urethra 97 or a vessel in which the balloon element is positioned so as to prevent an inadvertent withdrawal of device 49 from the body vessel and/or cavity.

With respect to the alternate constructions of the tubular device of the invention as shown in FIG. 16, it should first be recognized that often the feeding opening (such as the through bottom hole in the bolus of the present invention and the side holes in the prior art Entroflex ® Feeding Tube manufactured and sold by Biosearch Medical Products, Inc. of Somerville, N.J. 08876) on occasion clog and close off due to mucous, gastric juices, or other accumulated obstructions built up around the opening including even the nutritional product being fed down the feeding tube. Under such conditions, the doctor or technician operating the device may aspirate in an attempt to clear the feeding tube. However, upon aspiration with the conventional prior art feeding tube and particularly when repeated frequently, air which is forcefully evacuated and sucked out of the feeding tube with a syringe causes the tubular walls to collapse toward each other (like a straw would when drinking every last drop), and the bolus can be carried upward and out of the pylonic and cardiac sphincter due to the vacuum condition in the tube. With the addition of a connector having one or more side feeding apertures and a through the bolus feeding hole as shown in FIG. 16, such disadvantage is avoided as the tube is precluded from collapsing as all of the air in the tube could not be evacuated. In such a structure, there is less chance of dislodging the tube and bolus when aspirating as one or more of the feeding holes in the connector and bolus which are at substantially different locations would less likely be clogged simultaneously, and therefore ongoing nutrition feeding and safer aspiration is more assured.

Also, a suitable ring 82' with an integral one-way check valve may also be included in any of the embodiments of the invention including that of FIG. 16. With such a valve element means provided in the feeding tube, if the nutrition pump fails or shuts off for any reason, such as by a power failure, or if the nutritional supplement runs out, and before an operator or therapist can supply more nutrition, acidic gastric juices in the gastrointestinal tract accumulate and travel up in and around the feeding tube. Thus, a burning-like sensation can occur in the patient's mouth which is irritating to the patient and creates a most unpleasant aftertaste (acid and other hearburn like tastes one gets after belching). With the inclusion of a one-way valve say in the bolus or even farther up the feeding tube, such as in a top cap or other conventional closure of the tube, one can prevent this objectional back flow phenomenon.

With the devices of the present invention, any obstructions, if occuring, could be readily discharged by re-introduction of the stylet to clear the passageway. Such a technique can be thus done without removal of the lumen which is not viable in the existing conventional enteral feeding tubes which comprise a solid bolus.

It should also be noted that although at least one side feeding hole is shown in the connector piece between the tubular element and the through bolus, the hole or holes may be directly provided in the walls of the tubular element in lieu of the connector, but such holes provided therein should then be preferably molded or otherwise made so as not to develop cracks and spread to form even greater apertures than the particular sized holes provided in the device.

Although the present invention has been described in some detail by way of illustration and example for purposes of clarity of understanding, it will, of course, be understood that various arrangements of the parts without departing from the scope of the invention as set forth in the following claims.

What is claimed is:

1. A tubular medical device for fluid feeding into or fluid drainage from a body cavity of a patient, comprising, in combination an elongated flexible primary tube having an open end,
   a secondary tube concentrically surrounding and spaced from said primary tube and extending between said open end and a position spaced from said open end, said secondary tube having a joining portion integral with said primary tube at said open end and sealably connected to said primary tube around said position,
   said secondary tube and said primary tube forming a sealed chamber, and
   a heavy substance means in said chamber for positioning said chamber and said open end in the body cavity of the patient.

2. A tubular medical device according to claim 1, wherein said secondary tube has an outer surface having a hydrophilic coating.

3. A tubular medical device according to claim 2, wherein said heavy substance means is a heavy metal.

4. A tubular device according to claim 3, wherein said heavy metal is mercury.

5. A tubular device according to claim 3, wherein said heavy metal is tungsten.

6. A tubular medical device according to claim 3, wherein said primary and secondary tubing are made of a radio opaque material.

7. A tubular medical device according to claim 6, wherein said radio opaque material is a urethane composition.

8. A tubular medical device according to claim 1, including one-way valve means for precluding back flow of gastric juices.

9. A tubular medical device according to claim 8, wherein said one-way valve means is a ring with a check valve disposed in said primary tube.

10. A tubular medical device according to claim 9, wherein said check valve and ring are integrally made of plastic and is secured to the bottom end of said primary tube.

11. A tubular medical device according to claim 1, including at least one side hole in said primary tube.

12. A tubular medical device according to claim 11, wherein said at least one side hole is provided in connector means between said primary tube and said sealed chamber.

13. A method of making a tubular medical device for fluid feeding into or fluid drainage from a body cavity of a patient, which comprises:
   (a) treating the inner surface of the front end portion of an elongated, flexible primary tube with a hydrophilic coating, said front end portion being heat expandable;
   (b) expanding said treated front portion by heating and pressing said front end portion into a secondary tube having a diameter greater than the diameter of the primary tube;
   (c) everting said secondary tube concentrically around and spaced from said primary tube, wherein said hydrophilic coating is carried over to the outer surface of said secondary tube, said primary tube and said secondary tube forming a chamber having an opening at the rear end of said secondary tube;
   (d) placing a heavy substance into said chamber for positioning the front end of the device in the body cavity of the patient; and
   (e) sealing the chamber at the opening by sealably joining the rear end of the secondary tube with the outer surface of the primary tube, wherein a tip element is formed.

14. A method of making a tubular medical device according to claim 13, wherein said heavy substance placed in said chamber is a heavy metal.

15. A method of making a tubular medical device according to claim 11, wherein said substance is mercury.

16. A method of making a tubular medical device according to claim 15, wherein said substance is tungsten.

17. A method of making a tubular medical device according to claim 11, wherein said primary tube and said secondary tube are radio opaque.

18. A method of making a tubular medical device according to claim 17, wherein said radio opaque material is a urethane composition.

19. A method of making and positioning a tubular medical device for fluid feeding into or fluid drainage from a body cavity of a patient, which comprises:
   (a) treating the inner surface of at least the front end portion of an elongated, flexible primary tube with a hydrophilic coating, the front end portion being heat expandable;
   (b) affixing an elongated flexible side tube having opposed inlet and outlet ends to the outer surfaces of the primary tube wherein the outlet end is spaced form the front end portion,
   (c) expanding the treated front end portion by heating and forming the front end portion into a secondary tube having a diameter greater than the diameter of the primary tube;
   (d) everting the secondary tube concentrically around and spaced from the primary tube, wherein the hydrophilic coating is carried over to the outer surface of the secondary tube, the primary tube and the secondary tube forming a chamber having an opening at the rear end of the secondary tube;
   (e) inserting a support ring into the front end of the primary tube and affixing said support ring with the inner surface of the primary tube, the support ring having an inner diameter approximately equal to the inner diameter of the primary tube,
   (f) sealing the chamber at the opening by sealably joining the rear end of said secondary tube with the outer surface of the primary tube, wherein a tip element is formed, ambient air being sealed in the chamber;
   (g) sealably joining the secondary tube with the side tube;
   (h) inserting the sealed chamber of the device via a body canal into a body cavity of a patient;
   (i) connecting the inlet end of the side tube to a source of pressurized air;
   (j) expanding the chamber to form a balloon tip of the device that positions the device in the body cavity and prevents the device from sliding from the body cavity into the body canal.

20. The method of claim 19, wherein the primary and secondary tubes are radio opaque.

21. The method of claim 20, further including the step of forming at least one side hole in the primary tube near the outlet end.

22. The method of claim 19, further including the step of positioning a one-way check valve with the support ring after step (e).

23. A tubular medical device for fluid feeding into or fluid drainage from a body cavity of a patient, comprising, in combination,
   an elongated flexible primary tube having an open end,
   a secondary tube concentrically surrounding and spaced from said primary tube and extending between said open end and a position spaced from said open end, said secondary tube having a joining portion integral with said primary tube at said open end and sealably connected to said primary tube around said position,
   said secondary tube and said primary tube forming a sealed chamber,
   said secondary tube being made of a flexible material,
   a side tube affixed to the outer surface of said primary tube, said side tube having inlet and outlet ends affixed to said primary tube, said outlet end being positioned in said chamber,
   a source of pressurized air connected to said inlet end, said secondary tube being expanded under pressure from said pressurized air wherein said chamber forms a balloon, and
   one-way valve means positioned at said open end of said primary tube for precluding back flow of liquid, said one-way valve means being a stiffening ring and a check valve positioned at said open end, said primary tube forming at least one side hole.

24. The device according to claim 23, wherein said secondary tube has an outer surface having a hydrophilic coating.

25. The device according to claim 24, wherein said primary tube forms at least one hole near said secondary tube.

* * * * *